United States Patent
Burkhardt et al.

(10) Patent No.: US 11,147,690 B2
(45) Date of Patent: Oct. 19, 2021

(54) SYSTEMS AND METHODS FOR PERFORMING SPINAL SURGERY

(71) Applicant: GLOBUS MEDICAL, INC., Audubon, PA (US)

(72) Inventors: Alex Burkhardt, Akron, PA (US); Adam Friedrich, Cinnaminson, NJ (US); William Tally, Athens, GA (US)

(73) Assignee: Globus Medical Inc., Audubon, PA (US)

(*) Notice: Subject to any disclaimer, the term of this patent is extended or adjusted under 35 U.S.C. 154(b) by 162 days.

(21) Appl. No.: 16/289,395

(22) Filed: Feb. 28, 2019

(65) Prior Publication Data
US 2019/0290450 A1 Sep. 26, 2019

Related U.S. Application Data

(60) Provisional application No. 62/636,216, filed on Feb. 28, 2018.

(51) Int. Cl.
*A61F 2/46* (2006.01)
*A61F 2/44* (2006.01)
*A61F 2/30* (2006.01)
*A61F 2/28* (2006.01)

(52) U.S. Cl.
CPC ............ *A61F 2/4611* (2013.01); *A61F 2/447* (2013.01); *A61F 2002/2835* (2013.01); *A61F 2002/3069* (2013.01); *A61F 2002/30579* (2013.01); *A61F 2002/4627* (2013.01); *A61F 2002/4629* (2013.01); *A61F 2002/4631* (2013.01)

(58) Field of Classification Search
CPC ..... A61B 17/70–7098; A61F 2/44–447; A61F 2/4611
See application file for complete search history.

(56) References Cited

U.S. PATENT DOCUMENTS

| | | | |
|---|---|---|---|
| 2005/0197702 A1* | 9/2005 | Coppes | A61F 2/441 623/17.12 |
| 2011/0301712 A1* | 12/2011 | Palmatier | A61F 2/4611 623/17.16 |
| 2014/0046445 A1* | 2/2014 | Brennan | A61B 17/7044 623/17.16 |
| 2015/0223947 A1* | 8/2015 | Lynn | A61F 2/447 623/17.16 |
| 2016/0235546 A1* | 8/2016 | Cheng | A61F 2/4465 |
| 2017/0172758 A1* | 6/2017 | Field | A61F 2/4611 |
| 2017/0209284 A1* | 7/2017 | Overes | A61F 2/4455 |
| 2019/0083283 A1* | 3/2019 | Sharifi-Mehr | A61F 2/4611 |

* cited by examiner

*Primary Examiner* — Nicholas J Plionis

(57) ABSTRACT

A revision instrument for positioning and securing an intervertebral implant in an intervertebral space between vertebrae is provided. The revision instrument includes a shaft having a body extending from a first end to a second end. A first port and a second port extend through the body of the shaft and a connection tool having a first end and second end is positioned within the first port. The connection tool extends through the first end of the shaft through the second end of the shaft. The first end of the connection tool includes a mating feature configured to couple with an expandable implant and the second end of the connection tool includes a rotation feature configured to rotate the connection tool to engage or disengage the connection tool with the expandable implant. The second port is configured to receive an expansion driver for expanding or compressing the expandable implant.

5 Claims, 6 Drawing Sheets

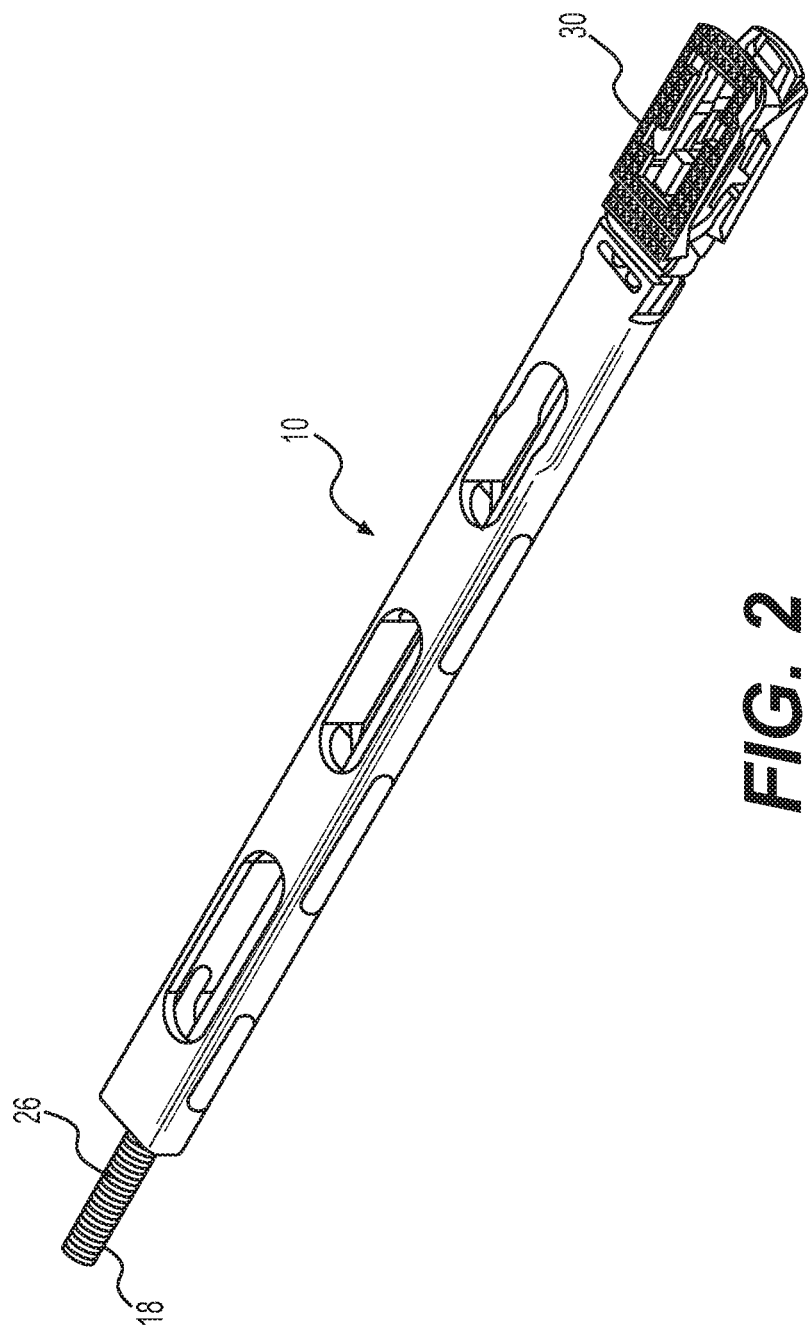

SYSTEMS AND METHODS FOR PERFORMING SPINAL SURGERY

CROSS REFERENCE TO RELATED APPLICATIONS

This application is a non-provisional application which claims priority to provisional application Ser. No. 62/636,216 filed on Feb. 28, 2018, which is incorporated in its entirety herein.

FIELD OF THE INVENTION

The present disclosure provides an instrument for more efficiently performing spinal surgery using expandable intervertebral implants.

BACKGROUND OF THE INVENTION

The vertebrate spine is the axis of the skeleton providing structural support for the other parts of the body. Adjacent vertebrae of the spine are supported by an intervertebral disc, which serves as a mechanical cushion permitting controlled motion between vertebral segments of the axial skeleton.

The spinal disc can be displaced or damaged due to trauma, disease, degenerative defects or wear over an extended period of time. To alleviate back pain caused by disc herniation or degeneration, the disc can be removed and replaced by an implant that promotes fusion of the remaining bone anatomy. The implant, such as a spacer or cage body, should be sufficiently strong to support the spine under a wide range of loading conditions. There remains a need for improved instrumentation that facilitate intervertebral fusion and serve as a means to restore intervertebral height and/or lordosis. Specifically, there is a need for instrumentation that allows for surgeons to control and manipulate an expandable implant throughout the entire procedure, regardless of patient positioning.

SUMMARY OF THE INVENTION

To meet this and other needs, intervertebral implants, instruments systems, and methods are provided. In one embodiment, a revision instrument for positioning and securing an intervertebral implant in an intervertebral space between vertebrae is provided. The revision instrument includes a shaft having a body extending from a first end to a second end. A first port and a second port extend through the body of the shaft and a connection tool having a first end and second end is positioned within the first port. The connection tool extends through the first end of the shaft through the second end of the shaft. The first end of the connection tool includes a mating feature configured to couple with an expandable implant and the second end of the connection tool includes a rotation feature configured to rotate the connection tool to engage or disengage the connection tool with the expandable implant. The second port is configured to receive an expansion driver for expanding or compressing the expandable implant.

In another embodiment, the present disclosure provides a spinal implant system for stabilizing adjacent vertebral bodies. The system includes an expandable implant and at least four pedicle screws, each of the at least four pedicle screws having a housing and configured to be positioned within the pedicle of the spine. The system includes at least two rods configured to be positioned within the housing of the pedicle screws. A revision instrument is also provided with includes a shaft having a body extending from a first end to a second end. A first port and a second port extending through the body of the shaft and a connection tool having a first end and second end positioned within the first port, the connection tool extends through the first end of the shaft through the second end of the shaft. The first end of the connection tool includes a mating feature configured to couple with an expandable implant and the second end of the connection tool includes a rotation feature configured to rotate the connection tool to engage or disengage the connection tool with the expandable implant. The second port is configured to receive an expansion driver for expanding or compressing the expandable implant.

In another embodiment, there is provided a method for stabilizing the spine of a patient that include the steps of providing an expandable implant and positioning the expandable implant in a disc space between adjacent vertebral bodies. The method also includes expanding the expandable implant to a first height within the disc space and attaching a revision instrument to the expandable implant and then securing the revision instrument to the patient. The method further includes transitioning the patient from a first position to a second position and positioning pedicle screws and rods in the posterior spine of the patient, engaging the revision instrument with an expansion driver to expand or compress the expandable implanter, securing and locking the pedicle screws and rods and removing the revision instrument from the patient.

BRIEF DESCRIPTION OF THE INVENTION

A more complete understanding of the present disclosure, and the attendant advantages and features thereof, will be more readily understood by reference to the following detailed description when considered in conjunction with the accompanying drawings wherein:

FIG. 2 illustrates the device of FIG. 1 attached to an expandable implant in one exemplary embodiment;

DETAILED DESCRIPTION OF THE INVENTION

Figure 1A:
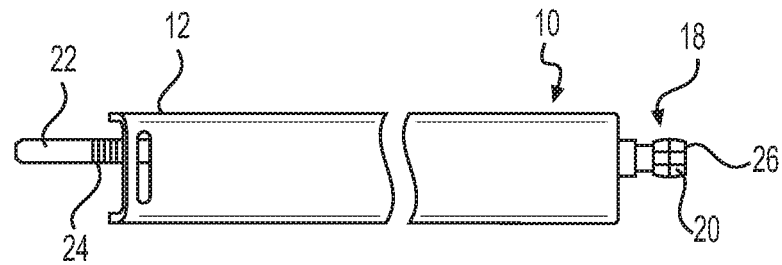
FIG. 1A is a top view of a revision instrument for performing spinal surgery using an expandable intervertebral implant.
Figure 1B:
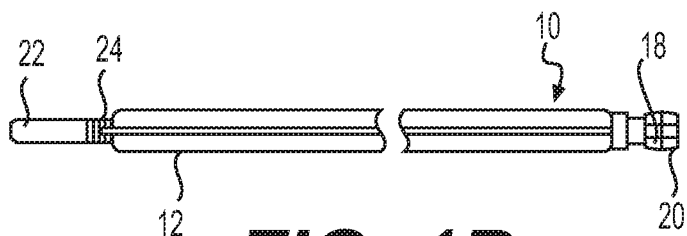
FIG. 1B is a side view of a revision instrument for performing spinal surgery using an expandable intervertebral implant.
Figure 1C:
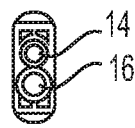
FIGS. 1C and 1D are a front view and a rear view of the revision instrument for performing spinal surgery using an expandable intervertebral implant.
Figure 1D:
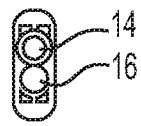

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

FIGS. 1A, 1B, 1C, and 1D illustrate a revision instrument 10 according to one exemplary embodiment of the invention. The revision instrument 10 for positioning and securing an intervertebral implant in an intervertebral space between vertebrae is provided. The revision instrument 10 includes a shaft 12 having a body extending from a first end to a second end. A first port 14 and a second port 16 extend through the body of the shaft and a connection tool 18 having a first end 22 and second end 20 is positioned within the first port 14. The connection tool 18 extends through the first end of the shaft through the second end of the shaft. The first end 22 of the connection tool includes a mating feature 24 configured to couple with an expandable implant and the second end of the connection tool 18 includes a rotation feature 26 configured to rotate the connection tool 18 to engage or disengage the connection tool 18 with the expandable implant. The second port 16 is configured to receive an expansion driver for expanding or compressing the expandable implant.

Figure 3:
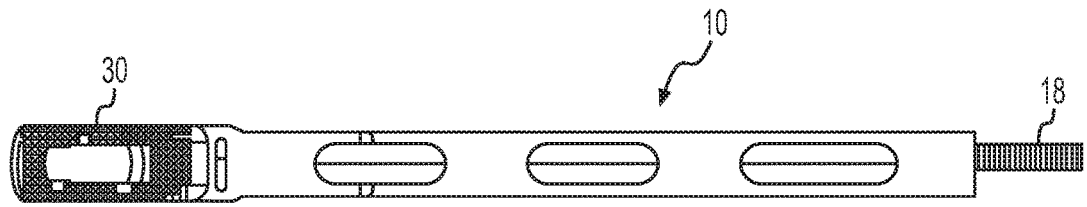
FIG. 3 is a top view of the revision instrument attached to an expandable implant.
Figure 4:
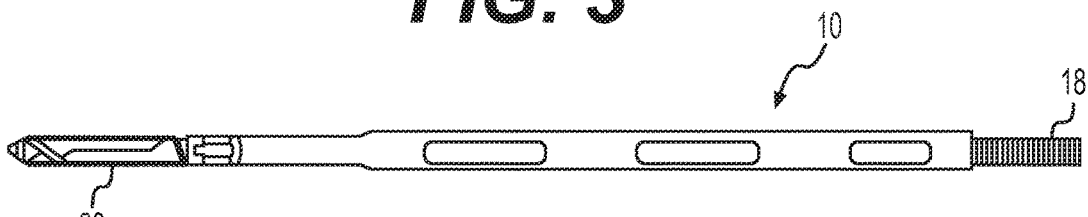
FIG. 4 is a side view of the revision instrument attached to the expandable implant shown in FIG. 3.

Now turning to FIGS. 2, 3, and 4, the revision instrument 10 coupled to an expandable implant 30 is illustrated. FIG. 2 illustrates a perspective view of the revision instrument 10 and the expandable implant 30, which is in an expanded state. FIG. 3 illustrates a top view of the revision instrument 10 attached to the expandable implant 30 and FIG. 4 illustrates a side view of the revision instrument 10 attached to the unexpanded expandable implant 30.

Figure 5:
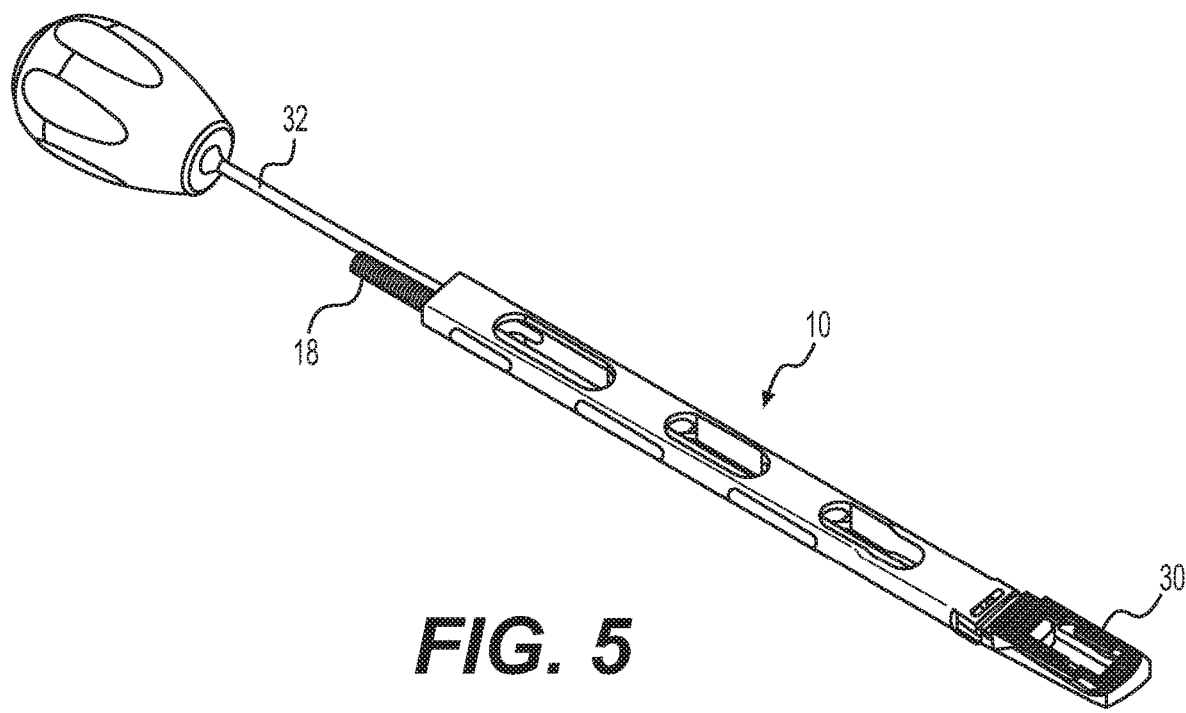
FIG. 5 illustrates the assembly of FIG. 2 in use with an expansion driver tool.

FIG. 5 illustrates the revision instrument 10 coupled to the expandable implant 30 and an expansion driver instrument 32. The expansion driver instrument 32 is used to either expand or collapse the expandable implant. The expansion driver instrument 32 is positioned through the second port of the revision instrument 10. The connection tool 18 is positioned through the first port of the revision instrument 10.

Figure 6:
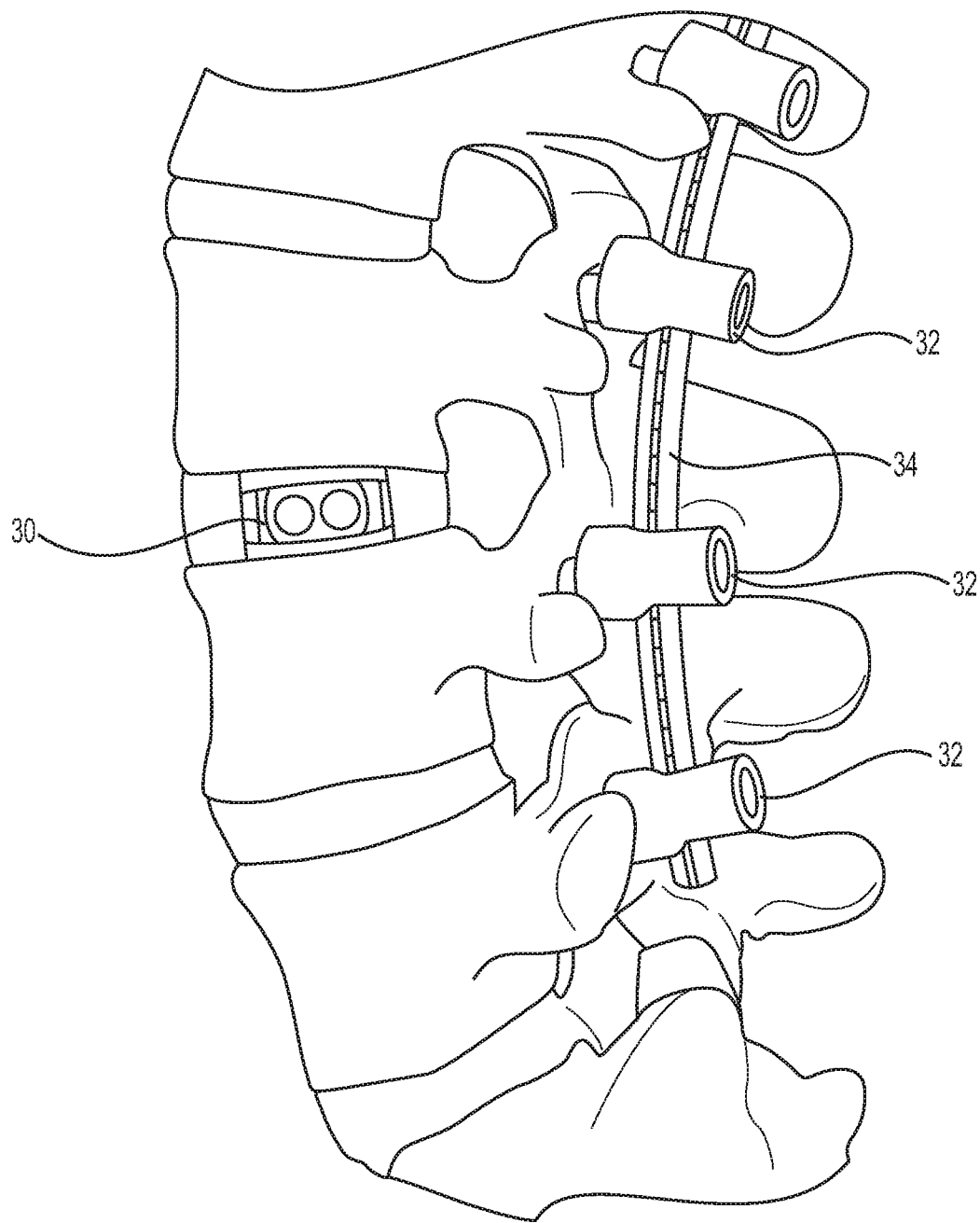
FIG. 6 illustrates a lateral view of an expandable implant positioned between adjacent vertebral bodies and posterior fixation implants.
Figure 7:
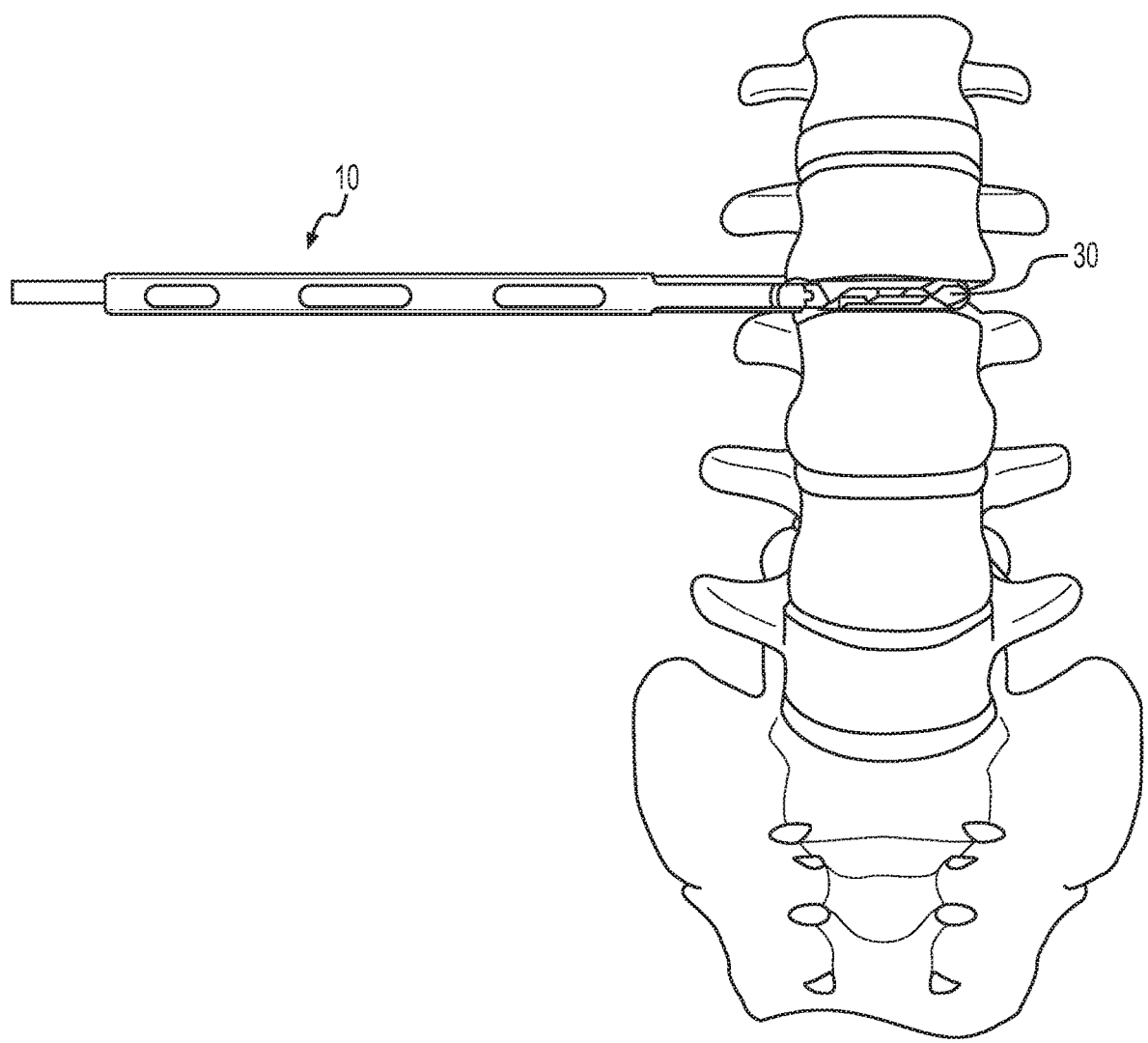
FIG. 7 illustrates the expandable implant coupled to the revision instrument for use in expanding the expandable implant.
Figure 8:
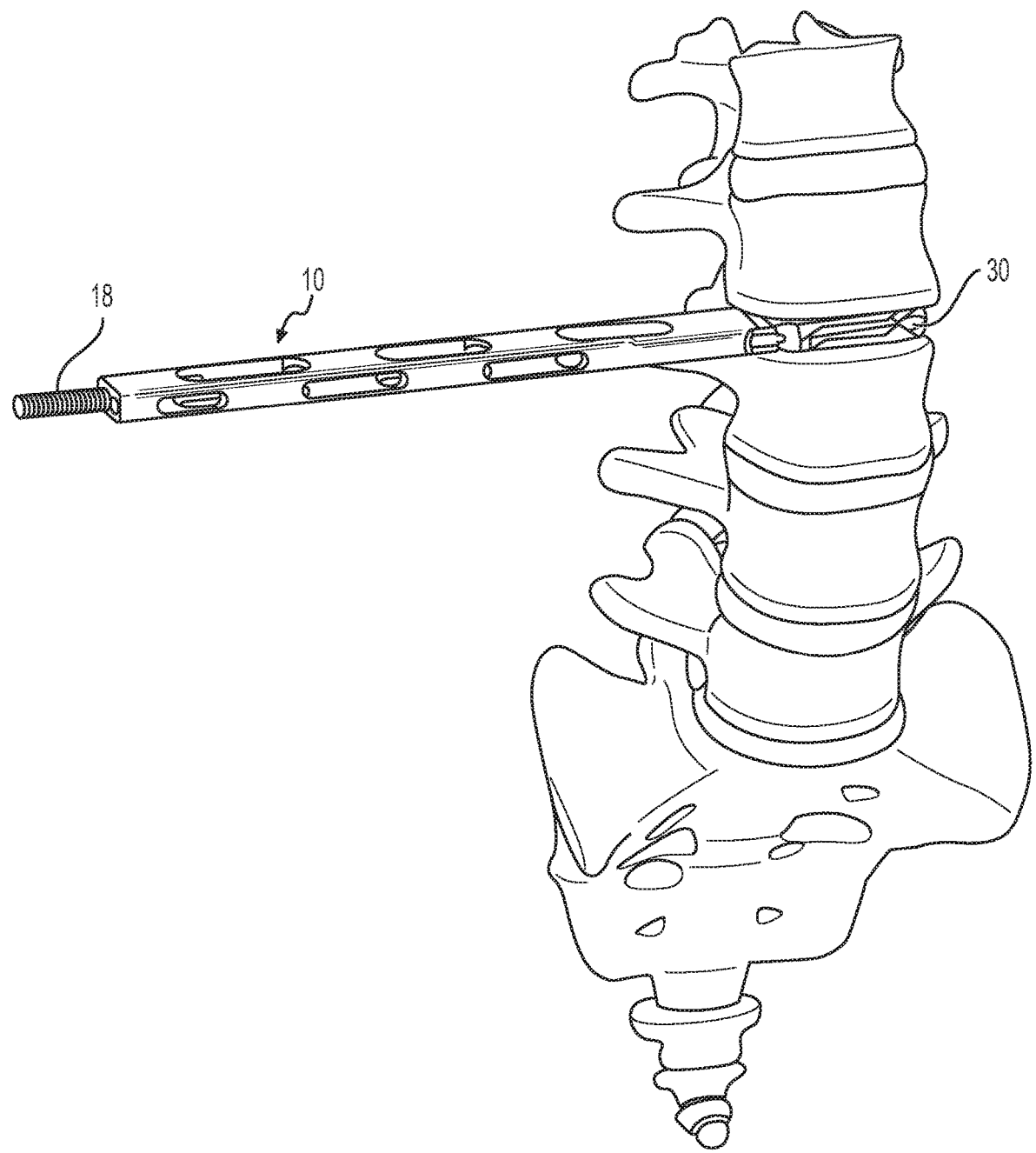
FIG. 8 illustrates an anterior view of the expandable implant coupled to the instrument.

Now turning to FIGS. 6, 7, and 8, the operation of the revision instrument with the expandable implant will be described in more detail. FIGS. 6, 7, and 8 illustrates an expandable implant 30 positioned within the intervertebral disc space. Also shown in FIG. 6 is posterior instrumentation that secures the mobility of the spinal segment. The posterior instrumentation includes pedicle screws 32 and rod 34 used to stabilize the posterior elements of the spine. During a spinal procedure to restore disc height and lordosis in the spine, surgeons may utilize the expandable implant 30 that may be inserted from a lateral approach to restore disc height and lordosis in a controlled manner. It should be noted that although a lateral implant is disclosed, anterior or posterior lateral expandable implants may also be used in the connection with the instrument of the present application. In these spinal procedures, the expandable implant 30 is positioned and then expanded until a maximum optimal height is reached or until a maximum input torque is applied. Factors that can limit the expansion of the implant 30 can include the mobility of the facet joints, excess disc material, and calcified ligaments. Once the expandable implant 30 is positioned between adjacent vertebral bodies, the patient is rotated to a position in which pedicle screws 32 and rod 34 may be placed to compress the instrumented segment in order to restore lordosis as shown in FIG. 6. It should be noted that although a single expandable implant is illustrated, additional expandable implants may be positioned in adjacent levels of the spine. As the spine is manipulated either through the positioning of additional interbody implants, posterior instrumentation (such as pedicle screws and rods), or repositioning on the surgical table, it may become necessary to adjust the expandable implant to compensate for increased mobility of the motion segments of the spine by utilizing the revision instrument 10.

As illustrated in FIGS. 6, 7, and 8, the revision instrument 10 may be used for additional expansion and/or adjustment of the interbody expandable implants at subsequent points in the procedure. The revision instrument 10 as discussed with reference to FIGS. 1-5, is positioned and retained to the expandable implant 20 in the surgical site and secured to the skin to allow for the patient to be repositioned and/or additional instrumentation to be placed. The revision instrument 10 would allow for the passing of the expansion driver tool 32 in order to manipulate the expandable implant 30 after additional interbody devices and/or posterior instrumentation are positioned in the posterior elements of the spine. The expandable implant 30 may then be adjusted to compensate for correction beyond that achieved from the initial patient positioning and expandable implant placement. The revision instrument can be secured to the patient to prevent excess forces on the implant-to-instrument connection.

In one exemplary embodiment, a method using the revision instrument with an expandable implant 30 as disclosed above is described below. The method includes the steps of providing an expandable implant and positioning the expandable implant in a disc space between adjacent vertebral bodies. The method also includes expanding the expandable implant to a first height within the disc space and attaching a revision instrument to the expandable implant and then securing the revision instrument to the patient. The method further includes transitioning the patient from a first position to a second position and positioning pedicle screws and rods in the posterior spine of the patient, engaging the revision instrument with an expansion driver to expand or compress the expandable implanter, securing and locking the pedicle screws and rods and removing the revision instrument from the patient.

In another embodiment, if any spondylolisthesis is present, it would be possible to decrease the expandable implant expansion while the patient is prone to allow for additional correction with posterior instrumentation. Once the desired correction of the spine is achieved, the implant can be re-expanded using the auxiliary instrument attached to the implant.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

We claim:

1. A method for stabilizing the spine of a patient comprising the steps of:
    providing an expandable implant;
    positioning the expandable implant in a disc space between adjacent vertebral bodies;
    expanding the expandable implant to a first height within the disc space;
    attaching a revision instrument to the expandable implant;
    securing the revision instrument to the patient;
    transitioning the patient from a first position to a second position;
    positioning pedicle screws and rods in the posterior spine of the patient;
    engaging the revision instrument with an expansion driver to expand or compress the expandable implant;
    securing and locking the pedicle screws and rods;
    removing the revision instrument from the patient;
    wherein the revision instrument includes a shaft having a body extending from a first end to a second end;
        a first port and a second port extending through the body of the shaft;
        a connection tool having a first end and a second end, the connection tool positioned within the first port, the connection tool extending through the first end of the shaft and through the second end of the shaft;
    wherein the first end of the connection tool includes a mating feature configured to couple with the expandable implant and the second end of the connection tool is configured to rotate the connection tool to engage or disengage the connection tool with the expandable implant,
    wherein the second port is configured to receive the expansion driver for expanding or compressing the expandable implant,
    wherein the expandable implant restores disc height and lordosis in the spine, and
    wherein the revision instrument is positioned and retained to the expandable implant in a surgical site and secured to the skin to allow for the patient to be repositioned.

2. The method of claim 1, wherein the mating feature of the connection tool includes a threaded feature and the step of attaching a revision instrument includes threading the threaded feature into the expandable implant.

3. The method of claim 1, wherein the mating feature of the connection tool is a dovetail connection.

4. The method of claim 1, further comprising receiving a graft delivery instrument in the second port and receiving graft material in the expandable implant through the received graft delivery instrument.

5. The method of claim 1, wherein the step of removing the revision instrument includes removing the revision instrument only after positioning the pedicle screws within pedicles of the spine.

* * * * *